(12) United States Patent
Sears et al.

(10) Patent No.: US 6,417,233 B1
(45) Date of Patent: Jul. 9, 2002

(54) UBIGUINONE-CONTAINING COMPOSITION SUITABLE FOR PROMOTING ENHANCED INTRAMITOCHONDRIAL TRANSPORTATION OF UBIGUINONES AND METHODS OF USING SAME

(75) Inventors: Grazia Sears, S. Maria Maddalena; Janos Feher, Montopoli di Sabina, both of (IT)

(73) Assignee: Sigma-Tau HealthScience S.p.A., Rome (IT)

( * ) Notice: Subject to any disclaimer, the term of this patent is extended or adjusted under 35 U.S.C. 154(b) by 0 days.

(21) Appl. No.: 09/807,918

(22) PCT Filed: Oct. 19, 1999

(86) PCT No.: PCT/IT99/00331

§ 371 (c)(1),
(2), (4) Date: May 23, 2001

(87) PCT Pub. No.: WO00/23069

PCT Pub. Date: Apr. 27, 2000

(30) Foreign Application Priority Data

Oct. 21, 1998 (IT) ......................................... BO98A0596

(51) Int. Cl.[7] ........................ A61K 31/22; A61K 31/20; A61K 31/12

(52) U.S. Cl. ......................... 514/549; 514/560; 514/689
(58) Field of Search .................................. 514/549, 560, 514/689

(56) References Cited

U.S. PATENT DOCUMENTS 5,895,652 A        4/1999   Giampapa

FOREIGN PATENT DOCUMENTS

| EP | 0 023 349 | 2/1981 |
|----|-----------|--------|
| EP | 0 325 244 | 7/1989 |
| WO | 32 24 619 | 5/1983 |
| WO | WO98/33476 | 8/1998 |

OTHER PUBLICATIONS

J. Karlsson E. A.: "Plasma omega–3 fatty acids before and after nutritional therapy" Journal of Nutritional & Environmental Medicine, vol. 8, No. 1, 1998, pp. 25–34.

*Primary Examiner*—Raymond Henley, Jr.
(74) *Attorney, Agent, or Firm*—Nixon & Vanderhye

(57) ABSTRACT

Compositions containing as active ingredients a lipid-soluble benzoquinone, e.g. Coenzyme Q10 and at least one omega-3 polyunsaturated fatty acid selected from eicosapentaenoic acid (EPA), docosahexaenoic acid (DHA) and linolenic acid (LNA), for the prevention and/or treatment of mitochondriopathies.

17 Claims, No Drawings

UBIGUINONE-CONTAINING COMPOSITION SUITABLE FOR PROMOTING ENHANCED INTRAMITOCHONDRIAL TRANSPORTATION OF UBIGUINONES AND METHODS OF USING SAME

This is A371 of PCT/IT99/00331 filed Oct. 19, 1999.

The present invention relates to a pharmaceutical/nutritional composition for supporting and/or providing therapy to individuals at risk and/or under treatment for dysfunctions of energy metabolism, and specifically, for mitochondrial diseases.

More specifically, the present invention relates to a composition comprising (a) an amount of a lipid-soluble benzoquinone selected from the group consisting of ubiquinone (Coenzyme $Q_{10}$, $CoQ_{10}$), its reduced form, ubiquinol-10 ($CoQ_{10}H_2$) or mixtures thereof, effective for performing a therapeutical and/or preventive and/or nutritional activity, and (b) at least a further component suitable for stimulating and enhancing the intramitochondrial transportation of component (a), the resulting composition being potently effective for the prevention and/or treatment of mitochondriopathies.

Accordingly the composition may take the form and exert the action of a dietary or nutritional supplement or of an actual medicine, depending upon the support or preventive action, or the strictly therapeutic action, which the composition is intended to exert in relation to the particular individuals it is to be used in. Depending on the actual circumstances, the composition of the present invention need not or, alternatively, should be taken under the supervision of an attending physician.

In the publication by the United Mitochondrial Disease Foundation, "About Mitochondria and Disease" (http://ibiochemgen.ucsd.edu/umdf/AboutMitoDisease.htm), which is incorporated herein by reference, the following definition of what a mitochondrial disease is, and what the triggering, sub-cellular causes are, is given:

"The mitochondria produce adenosine triphosphate (ATP), the body's mobile energy source. When mutations occur which affect the mitochondria, the vital supply of ATP is disrupted, less and less energy is generated within the cell. When this process is repeated on a large scale throughout the body, whole systems begin to fail, and the life of the person in whom this is happening can be compromised, changed or even ended. The cells that require the most energy, like the brain, heart and skeletal muscles, are the most vulnerable".

This reference also provides a detailed list and description of mitochondrial diseases, which encompasses, inter alia, Co-enzyme $Q_{10}$ deficiency; Complex III deficiency (Ubiquinone—cytochrome c oxidoreductase deficiency) whose symptoms include pigmentary retinopathy; Complex IV deficiency/COX deficiency (cytochrome c oxidase deficiency) whose symptoms include optic atrophy and ophthalmoplegia; CPEO (Chronic Progressive External Ophthalmoplegia Syndrome) whose symptoms include visual myopathy and retinis pigmentosa; ARMD (Age-Related Macular Degeneration); NARP (Neuropathy, Ataxia and Retinis pigmentosa) and many others.

Since $CoQ_{10}$ is indispensable to cellular bioenergetics, its deficiency may bring about a host of pathologies.

Indeed, $CoQ_{10}$ is known to play an essential role as an electron (redox) carrier in the mitochondrial electron transport chain of the cell. However, it also protects membrane phospholipids and those in LDL from peroxidation as well as protects and/or regenerates vitamin E. $CoQ_{10}$ is synthesized in the body from precursors of cholesterol synthesis and therefore is not classed as a vitamin. However, the ability to synthesize $CoQ_{10}$ decreases with age and there may be an increasing dependence on food to supply the nutrient. The most abundant sources are fresh unprocessed foods, particularly meats, fish, nuts and seed oils. The average daily intake of $CoQ_{10}$ is approximately 2 mg.

Ubiquinol-10 or $CoQ_{10}H_2$, the reduced form of $CoQ_{10}$, plays a second role as a potent lipid-soluble antioxidant and its activity at physiological concentrations in the lipid components of cells has recently been shown.

$CoQ_{10}$'s antioxidative, electron transport, and membrane-stabilizing properties have widely been investigated aiming at prevention of and/or treatment of various cardiovascular diseases, including prevention of cellular damage during reperfusion, angina pectoris, hypertension, myocardial ischemia, and congestive heart failure.

In patients with mitochondrial encephalomyopathy, $CoQ_{10}$ treatment increases mitochondrial functions and exercise performance, and reduces the acidosis associated with exercise. This finding is consistent with $CoQ_{10}$ participation in electron transport and mitochondrial membranes, and in the biological oxidation of cellular fuels for energy generation.

$CoQ_{10}$ deficiency was also reported to be associated with viral infections, and supplementation of $CoQ_{10}$ in acquired immune deficiency syndrome (AIDS) patients resulted in enhanced macrophage activity and increased serum level of IgG. $CoQ_{10}$ treatment has been reported to provide some benefits in cancer patients, and enhanced hematopoietic activity in malnourished children. All the evidence suggests that $CoQ_{10}$ may play essential roles in maintaining and promoting health, under normal and abnormal conditions.

It has become more and more apparent that individuals at risk and/or under treatment for mitochondriopathies are in need of increased supplementation of ubiquinones with respect to the normal intake of these substances through the diet, since particularly $CoQ_{10}$ deficiency may cause the onset, precipitate or aggravate the symptoms of a serious mitochondriopathy.

Many efforts have been made over the last decade in order to find formulations that would increase the bioavailability of $CoQ_{10}$ or anyhow enhance its efficacy at the cellular organelle sites of action. For instance, M. Weis et al in "Bioavailability of four oral Coenzyme $Q_{10}$ formulations in healthy volunteers (Molec. Aspects Med. Vol. 15 [supplement] pps 273-s 280, 1994) report on a four-way randomised cross-over trial wherein the bioavailability of four different $CoQ_{10}$ formulations was compared. The study results suggest that a soy bean oil suspension of $CoQ_{10}$ (Bioquinon®, 100 mg $CoQ_{10}$ with 400 mg of soy bean oil in soft gelatine capsules) exhibits the highest bioavailability.

However, in spite of all these efforts, no satisfactory formulations able to provide a therapeutical or preventive effective concentration of ubiquinons and particularly of $CoQ_{10}$ at their intracellular sites of action, have been developed to-date.

Polyunsaturated fatty acids (PUFA) are subdivided in classes based on the location of the first double bond counting from the methyl end of the fatty acid molecule: ω-3 (or n-3) fatty acids have their first double bond between the third and fourth carbon atoms, and the (ω-6 (or n-6) fatty acids have their first double bond between the sixth and seventh carbon atoms. Particularly importante are the ω-3 fatty acids and, specifically, linolenic acid (18:3 ω3) (LNA), eicosapentaenoic acid (20:5 ω3) (EPA), and docosahexaenoic acid (22:6 ω3) (DHA), wherein the first number (before the colon) gives the number of carbon atoms in the molecule and the second gives the number of double bonds.

In the last two decades, epidemiologic studies, clinical investigations and animal experiments have expanded our knowledge of the properties of dietary fatty acids in health and disease, growth and development. As a recent result of these investigations, the focus is on the ratio of ω-6/ω-3 fatty acids in the diet; the essentiality of ω-3 fatty acids and their metabolic effect in the prevention and treatment of chronic diseases. These biological and functional effects of ω-3 fatty acid exert profound beneficial metabolic changes in coronary heart disease, hypertension, non-insulin-dependent diabetes mellitus, inflammatory and autoimmune disorders, and possibly cancer. For a detailed account on the sources, metabolism, biological and functional effects and dietary aspects of ω-3 fatty acids see e.g. "Functional Food" edited by Israel Goldberg, Chapman & Hall (1994), Chapter 16: "Fatty Acids" by Artemis P. Simopoulos, pp 355–392, which is incorporated herein by reference.

We have now found that a combination composition comprising in admixture:

(a) a lipid soluble benzoquinone selected from the group consisting of Coenzyme $Q_{10}$, ($CoQ_{10}$), its reduced form, ubiquinol-10 ($CoQ_{10}H_2$) or mixtures thereof, in an amount effective for performing a therapeutical and/or preventive and/or nutritional activity in a human need thereof; and (b) at least one omega-3 polyunsaturated fatty acid or an ester thereof, is able to enhance the pharmacological/nutritional effects of $CoQ_{10}$ and/or $CoQ_{10}H_2$.

Although it is neither intended nor necessary to rely on any theoretical interpretation to account for the aforesaid enhanced effects, it is apparent that, most likely, they are due to the omega-3 poly-unsaturated acid acting as bioactive vehicles for $CoQ_{10}$ and/or $CoQ_{10}H_2$ and boosters of the intramitochondrial transportation thereof to their sites of action.

The omega-3 polyunsaturated acid is selected from the group consisting of eicosapentaenoic acid (EPA), docosahexaenoic acid (DHA), linolenic acid (LNA) or mixtures thereof. EPA and DHA or mixtures thereof are particularly preferred. Preferred esters of LNA, EPA or DHA are the triglycerides and the ethyl ester.

The composition may also comprise saturated, monoinsaturated, omega-6 and omega-9 fatty acids or mixtures thereof. Examples of such acids are palmitic acid (16:0), oleic acid (18:1 ω9), linoleic acid (18:2 ω6), and arachidonic acid (20:4 ω6) or mixture thereof. If one or more of these non omega-3 fatty acids are present, the amount of the aforesaid omega-3 fatty acids, particularly EPA and/or DHA, preferably exceeds 65% and is lower than 95% by weight of the overall mixture of omega-3 fatty acids.

The weight ratio DHA:EPA in the composition ranges from 1:1 to 1:20, preferably from 1:1 to 1:5.

The weight ratio (b):(a) in the compostion ranges from 1:20 to 1:50.

The composition of the present invention may further comprise α-tocopherol (vitamin E) as component (c). Preferably, the weight ratio (b):(c) in the composition ranges from 1:20 to 1:50. We have found that the aforesaid omega-3 fatty acids act as bioactive vehicles towards Vitamin E as well, i.e. they enhance the parmacological effects of Vitamin E.

The efficacy of the compositions according to the present invention towards many forms of mitochondriopathies and the ability of the same compositions to enhance the intramitochondrial transportation of $CoQ_{10}$ was shown in clinical trials. As an istance of the successful treatment of a mitochondriopathy, a study on patients affected by photophobia and ARMD is reported hereinbelow.

The following retinal model for assessing mitochondriopathy was used.

As known, reactive oxigen species (ROS) may be generated at least at three sites in the retina:

in the photoreceptor cell during light stimulation.

in the retinal pigmented epithelium (RPE), which phagocitize photoreceptor discs during normal turnover and light stimulation.

in the neuroretina at the synaptosomes.

In each of these three sites, mitochondria are the common source and target of ROS.

We found that in the normal retina, mitochondrial membranes of the photoreceptor cells have significantly different molecular structure than those of the outer segment discs. The mitochondrial membranes are more basophilic, and they contain more unsaturated lipids than the disc membranes of the outer segments. Further, in vitro studies of normal human photoreceptors cells showed, that the behaviour of mitochondrial and disc membranes is different when they are exposed to oxido-reductive stress. The same oxidative stress which resulted in reversible alteration of the disc membranes, caused irreversible damage of the mitochondrial membranes. However, the exposure to strong electron donor substances (chlorpromazines) slightly altered the structure of mitochondrial membranes, but it disrupted the disc membranes in dose dependent manner. These findings suggested that mitochondrial membranes are more sensible to oxidative, while disc membranes are more sensible to reductive influences.

Via electron microscopic studied on diseased human retinas, we showed that mitochondrial damage is a typical alteration in age-related macular degeneration (ARMD), myopic retinal dystrophies (NRD) and in retinitis pigmentosa (RP). Mitochondrial alterations included loss of the cristae, accumulation of intramitochondrial lipid droplets, swollen of the mitochondria, and decrease in number of them were observed in diseased RPE and photoreceptors cells. Pigment epithelial cells were predominantly affected in ARMD and MRD, while in RP both photoreceptor and pigmented epithelial cells were seriously altered.

These findings suggested that the retina is a suitable model for assessing mitochondriopathy.

We performed open, controlled studies of the various compositions of $CoQ_{10}$ and alpha tocopherol with or without the addiction of omega-3 fatty acids. In each series of healthy volunteers and photophobia patients the treatment was applied for one month, while in the series of ARMD patients it was for three months. To evaluate visual function before and after treatment, as well as after one month of "wash-out" macular photostress test was applied.

Macular Photostress Test: 60 seconds bright light illumination to one eye (the follow eye was covered) by standardized slit lamp (full aperture and maximum intensity of a Haag-Streit slit lamp). Contrast sensitivity was tested by Maffei decimal chart before and after the illumination and the recovery time was measured (i.e. measured the time when the eye was able to read the same figure, as before the photostress). This function of the retina depends on the metabolic support to light stimulation-regeneration, thus a very suitable method for evaluate mitochondrial functions (Wu, G., Weiter, J. J., Santos, S., Ginsburg, L., Villalobos, R.: The macular photostress test in diabetic retinopathy and age-related macular degeneration. Arch. Ophthalmol., 108, 1556–58 (1990).

Blood levels of total, HDL, and LDL cholesterol and triglicerid levels were evalutated before, after three months of treatment, and after one month "wash-out" in the ARMD group.

a) Healthy Volunteers 12 healthy volunteers were enrolled in this clinical trial (6 male, 6 female, aged 24–37 years, mean body weight 66,5 kg).

$1^{st}$ group: treated with 50 mg $CoQ_{10}$ granulated+70 mg vitamin E/day $2^{nd}$ group: treated with 100 mg $CoQ_{10}$ granulated+70 mg vitamin E/day $3^{rd}$ group: treated with 30 mg $CoQ_{10}$ in soy bean oil+30 mg vitamin E/day $4^{th}$ group: treated with 30 mg $CoQ_{10}$ in omega-3 (>65% conc.)+30 mg Vitamin E/day Results healthy volunteers react very poorly to these treatments;

pharmacological effect of 50 mg $CoQ_{10}$ granulated+ vitamin E was insignificant;

lipid addition improved dose-efficacy relation of $CoQ_{10}$+vitamin E (100 mg. $CoQ_{10}$ granulated were equivalent 30 mg of $CoQ_{10}$ dissolved in soy bean oil);

highly concentraded PUFA was the most effective treatment.

b) Photophobia Patients 16 patients suffered from photophobia were entrolled in this trial (11 female, 5 male, aged 23–44 years, mean body weight 63,4 kg).

$1^{st}$ group: treated with 100 mg $CoQ_{10}$ granulated+70 mg vitamin E/day $2^{nd}$ group: treated with 30 mg $CoQ_{10}$ in soy bean oil+30 mg vitamin E/day $3^{rd}$ group: treated with 30 mg $CoQ_{10}$ in fish oil (>30% conc.)+30 mg vitamin E/day $4^{th}$ group: treated with 30 mg $CoQ_{10}$ in omega-3 (>65% conc.)+30 mg Vitamin E/day Results The pharmacological effect of $CoQ_{10}$+vitamin E was approximately double in cases of photophobia than in healthy volunteers.

omega-3 enhances intensity and duration of the parmacological effects of $CoQ_{10}$+vitamin E;

higher concentration of omega-3 was showed better effects than lower concentration: the differences were 50% after one month of treatment, and approximately 30% after one month of "wash-out".

c) Retinal Distrophy Patients 43 patients affected by early age-related macular degeneration (visual acuity better than 20/40) were involved in these studies (23 female, 20 male, aged between 55–66 years, mean body weight 66,8 kg).

$1^{st}$ group: treated with lutein+zeaxantin+vitamin E (a commercially available product)

$2^{nd}$ group: treated with 1.000 mg omega-3 (>65%) only $3^{rd}$ group: treated with fish oil+30 $CoQ_{10}$+30 mg vitamin E/day $4^{th}$ group: treated with omega-3 (>65%)+30 mg $CoQ_{10}$+ 30 mg Vitamin E/day Results There were no significant differences between the groups treated with a commercially available dietary supplement (containing lutein, zeaxantin and vitamin E) and omega-3 (>65%) alone.

$CoQ_{10}$+vitamin E in highly concentrated omega-3 was more effective than fish oil+$CoQ_{10}$+vitamin E, after 3 months (50%) and after one month of wash-out (30%);

highly concentrated (>65%) PUFA showed synergistics pharmacological effects with $CoQ_{10}$ and vitamin E, superior than those of low concentration PUFA or saturated lipids;

highly concentrated (>65%) PUFA administration showed lowering of the plasma triglyceride levels and improved the ratio of total/HDL cholesterol, which was not observed in fish oil (30% omega-3) treated cases. In contrary, in 3 of the 12 cases, increase of total cholesterol and/or triglicerid levels were observed.

TABLE I

Healthy volunteers

|  | Treatment | Wash-out |
|---|---|---|
| 50 mg $CoQ_{10}$ gran + 70 mg vit. E | 0,9% | 0,5% |
| 100 mg $CoQ_{10}$ gran + 70 mg vit. E | 4,3% | 0,9% |
| 30 mg $CoQ_{10}$ + 30 mg vit. E + soy bean oil | 5,7% | 0,6% |
| 30 mg $CoQ_{10}$ + 30 mg vit. E + 858 mg omega-3 | 7,2% | 2,4% |

TABLE II

Photophobia patients

|  | Treatment | Wash-out |
|---|---|---|
| 100 mg $CoQ_{10}$ gran + 70 mg vit. E | 6,4% | −2,3% |
| 30 mg $CoQ_{10}$ + 30 mg vit. E + soy bean oil | 7,3% | −1,2% |
| 30 mg $CoQ_{10}$ + 30 mg vit. E + 1.000 mg fish oil | 9,4% | 3,1% |
| 30 mg $CoQ_{10}$ + 30 mg vit. E + 858 mg omega-3 | 18,1% | 9,4% |

TABLE III

Age-Related Macular Degeneration

|  | Treatment | Wash-out |
|---|---|---|
| Lutein - Zeaxantin - mg vit. E | 6,2% | −0,8% |
| 1.000 mg omega-3 | 7,0% | 1,0% |
| 30 mg $CoQ_{10}$ + 30 mg vit. E + 1.000 mg fish oil | 7,8% | 2,1% |
| 30 mg $CoQ_{10}$ + 30 mg vit. E + 858 mg omega-3 | 15,1% | 7,3% |

Conclusions

These pharmacological studies showed that $CoQ_{10}$+vitamin E in a vehicle of highly concentrated polyunsaturated fatty acids improved retinal function, primarily the regeneration of photoreceptor cells in normal conditions and in diseases states.

The most likely cellular target of these substances is the mitochondria of photoreceptor cells. The longer duration of visual improvement, a particularly important pharmacological effect, indicates that the composition of the present invention achieves a higher intracellular concentration of $CoQ_{10}$ and/or higher affinity of this substance to the target organelles than those accomplished via the usual enterally administrable $CoQ_{10}$-containing formulations at present commercially available.

The following examples of compositions are offered by way of illustration only and not by way of limitation.

EXAMPLE 1
700 mg (*) Soft Gelatine Capsule

| | |
|---|---|
| Eicosapentaenoic acid (EPA) | 148.72 mg |
| Docosahexaenoic acid (DHA) | 105.82 mg |
| Linolenic acid (LNA) | 31.46 mg |
| Coenzyme $Q_{10}$ | 10.00 mg |
| Proteins | 137.00 mg |
| Carbohydrates | 63.00 mg |

EXAMPLE 2
1,420 mg (*) Soft Gelatine Capsule

| | |
|---|---|
| Eicosapentaenoic acid (EPA) | 340 mg |
| Docosahexaenoic acid (DHA) | 240 mg |
| Linolenic acid (LNA) | 70 mg |
| Coenzyme $Q_{10}$ | 20 mg |
| Vitamin E | 20 mg |
| Proteins | 300 mg |
| Carbohydrates | 150 mg |

(*) The balance to 700 mg (or 1,420 mg, respectively) is accounted for considering that the omega-3 fatty acids are present as triglycerides.

What is claimed is:

1. A combination composition consisting essentially of in admixture the following components:
   (a) a lipid-soluble benzoquinone selected from the group consisting of Coenzyme $Q_{10}$ (Co$Q_{10}$), its reduced form, ubiquinol-10 (Co$Q_{10}H_2$) or mixtures thereof, in an amount effective for a therapeutic and/or preventive and/or nutritional activity in a human in need thereof, and
   (b) at least one omega-3 polyunsaturated fatty acid or an ester thereof, in an amount effective for enhancing the pharmacological/nutritional effects of said benzoquinone, wherein the omega-3 poly-unsaturated fatty acid is selected from the group consisting of eicosapentaenoic acid (EPA), docosahexaenoic acid (DHA) and mixtures thereof, wherein a non omega-3 fatty acid selected from a saturated, monosunsaturated, omega-6 fatty acid, omega-9 fatty acid and mixtures thereof or one or more additives selcted from the group consisting of vitamins, mineral salts, atioxidizing agents, amino acids, polysaccharides and vegetable fibers are optionally present.

2. The composition of claim 1, wherein the ester of eicosapentaenoic or docosahexaenoic acid is a triglyceride or an ethyl ester.

3. The composition of claim 1 wherein a saturated, monounsaturated, omega-6 fatty acid, omega-9 fatty acid and mixtures thereof is present.

4. The composition of claim 3, wherein the non omega-3 fatty acid is selected from the group consisting of palmitic acid, oleic acid, linoleic acid, arachidonic acid and mixtures thereof.

5. The composition of claim 4, wherein the amount of the omega-3 fatty acid exceeds 65% by weight of the overall mixture of omega-3 and non omega-3 fatty acids.

6. The composition of claim 5, wherein the amount of the omega-3 fatty acid is less than 95% by weight of the overall mixture of omega-3 and non omega-3 fatty acids.

7. The composition of claim 1, wherein the weight ratio DHA:EPA ranges from 1:1 to 1:20.

8. The composition of claim 7, wherein the weight ratio DHA:EPA ranges from 1:1 to 1:5.

9. The composition of claim 1, wherein the weight ratio (b):(a) ranges from 1:20 to 1:50.

10. The composition of claim 1, further comprising (c) α-tocopherol (vitamin E).

11. The composition of claim 10, wherein the weight ratio (b):(c) ranges from 1:20 to 1:50.

12. The composition of claim 1 wherein one or more additives selected from the group consisting of vitamins, mineral salts, anioxidizing agents, amino acids, polysaccharides and vegetable fibers are present.

13. The composition of claim 1 in solid, semisolid, liquid, semiliquid, powder, granular or liposomic form, and occurring as tablets, capsules, granulates, powders and vials for the oral or parenteral administration.

14. A method of treating a mitrochondrial condition or disease comprising administering to a human subject a combination of:
   (a) a lipid-soluble benzoquinone selected from the group consisting of Coenzyme $Q_{10}$ (Co$Q_{10}$), its reduced form, ubiquinol-10 (Co$Q_{10}H_2$) or mixtures thereof, in an amount effective for therapeutic and/or preventive and/or nutritional activity in a human in need thereof, in admixture with
   (b) at least one omega-3 polyunsaturated fatty acid or an ester thereof.

15. The method of claim 14, wherein said condition is a mitochondriopathy.

16. The method of claim 15, wherein the mitochondriopathy is selected from Coenzyme $Q_{10}$ deficiency; ubiquinone—cytochrome c oxidoreductase deficiency; cytochrome c oxidase deficiency; chronic progressive external ophthalmoplegia syndrome; age-related macular degeneration, neuropathy, ataxia and retinis pigmentosa.

17. The method of claim 14, wherein the nutritional/pharmacological combination further includes Vitamin E.

* * * * *